United States Patent
Har-Noy

(10) Patent No.: US 10,272,143 B2
(45) Date of Patent: Apr. 30, 2019

(54) TREATMENT OF HUMAN IMMUNODEFICIENCY VIRUS/ACQUIRED IMMUNODEFICIENCY SYNDROME

(71) Applicant: Immunovative Therapies Ltd., Jerusalem (IL)

(72) Inventor: Michael Har-Noy, Jerusalem (IL)

(73) Assignee: IMMUNOVATIVE THERAPIES LTD., Jerusalem (IL)

( * ) Notice: Subject to any disclaimer, the term of this patent is extended or adjusted under 35 U.S.C. 154(b) by 0 days.

(21) Appl. No.: 14/592,701

(22) Filed: Jan. 8, 2015

(65) Prior Publication Data

US 2015/0190488 A1 Jul. 9, 2015

Related U.S. Application Data

(60) Provisional application No. 61/924,936, filed on Jan. 8, 2014.

(51) Int. Cl.
| | | |
|---|---|---|
| A61K 39/21 | (2006.01) |
| A61K 39/00 | (2006.01) |
| A61K 45/06 | (2006.01) |
| A61K 35/17 | (2015.01) |

(52) U.S. Cl.
CPC .......... *A61K 39/0005* (2013.01); *A61K 35/17* (2013.01); *A61K 45/06* (2013.01)

(58) Field of Classification Search
None
See application file for complete search history.

(56) References Cited

U.S. PATENT DOCUMENTS

| 6,579,521 B2 | 6/2003 | Sahner |
| 2002/0022034 A1 | 2/2002 | Lisziewicz |
| 2006/0079443 A1 | 4/2006 | Ilan et al. |
| 2010/0086561 A1 | 4/2010 | Har-Noy |
| 2012/0128656 A1 | 5/2012 | Har-Noy |

FOREIGN PATENT DOCUMENTS

| JP | 2002-543144 A | 12/2002 | |
| JP | 2007-523884 A | 8/2007 | |
| JP | 2013-523886 A | 6/2013 | |
| WO | 2005084276 A2 | 9/2005 | |
| WO | 2010/0039924 A2 | 4/2010 | |
| WO | 2010051521 A1 | 5/2010 | |
| WO | 2011077100 A1 | 6/2011 | |
| WO | WO 2011/084451 A2 * | 7/2011 | ............. A61K 38/19 |
| WO | 2011117408 A1 | 9/2011 | |
| WO | 2011/130247 A2 | 10/2011 | |

OTHER PUBLICATIONS

Kreuter and Wieland Human papillomavirus-associated diseases in HIV-infected men who have sex with men. Curr Opin Infect Dis 22:109-114.*
Dorrell et al. Safety and tolerability of recombinant modified vaccinia virus Ankara expressing an HIV-1 gag/multiepitope immunogen (MVA.HIVA) in HIV-1-infected persons receiving combination antiretroviral therapy. Vaccine. 2007; 25(17):3277-3283.*
Haynes and McElrath. Progress in HIV-1 Vaccine Development. Curr Opin HIV AIDS. Jul. 2013 ; 8(4): 326-332.*
Hanke and McMichael 2000. Nature Medicine 6(9):951-955.*
Pett and Emery, Immunomodulators as adjunctive therapy for HIV-1 infection, J. Clin. Virol. 2001; 22: 289-295.*
Patel et al. Incidence of Types of Cancer among HIV-Infected Persons Compared with the General Population in the United States, 1992-2003. Ann. Intern. Med. 2008; 148L 728-738.*
Hirsch et al. Immune Reconstitution in HIV-Infected Patients. Clin. Infect. Dis. 2004; 38: 1159-1166SL Pett, Immunotherapies in HIV-1 infection. Curr. Opin. HIV AIDS, 2009; 4: 188-193.*
SL Pett, Immunotherapies in HIV-1 infection. Curr. Opin. HIV AIDS, 2009; 4: 188-193.*
Smith and Housseau, An Unexpected Journey: How Cancer Immunotherapy Has Paved the Way for an HIV-1 Cure. Disc. Med. 2015; 1-8.*
Thiébaut et al. Repeated Cycles of Recombinant Human Interleukin 7 in HIV-Infected Patients With Low CD4 T-Cell Reconstitution on Antiretroviral Therapy: Results of 2 Phase II Multicenter Studies. Clin. Infect. Dis. 2016; 62(9): 1179-85.*
Bernstein et al. Immune reconstitution following autologous transfers of CD3/CD28 stimulated CD4+ T cells to HIV-infected persons. Clin. Immunol. 2004; 111: 262-274.*
Gorenec et al. "The comparison of Th1, Th2, Th9, Th17 and Th22 cytokine profiles in acute and chronic HIV-1 infection". Micob. Pathogen. 2016; 97:125-130.*
Immunovative Announces Regulatory Clearance to Conduct a Phase II/III Clinical Trial in Advanced Metastatic Breast.Cancer for AlloStim(tm), Immunovative, Inc., Nov. 29, 2012, Retrieved from the Internet: http://www.immunovativeinc.com.
Sawka CA et al. "A prospective, non-randomised phase 1-2 trial of VACOP-B with filgrastim support for HIV-related non-Hodgkin's lymphoma", Biotechnol Annu Rev., 2005; 11, pp. 381-389, abstract, retrieved from PubMed, PMID:16216784.
Kornbluth R.S. "The emerging role of CD40 ligand in HIV infection", Journal of Leukocyte Biology, Sep. 2000, vol. 68, No. 3, p. 373-382.
International Search Report for International Patent Application No. PCT/US2015/010658, dated Jun. 4, 2015.
Written Opinion of the International Searching Authority for International Patent Application No. PCT/US2015/010658, dated Jun. 4, 2015.
Rusconi, S., P. Vitiello, et al. (2013). "Maraviroc as intensification strategy in HIV-1 positive patients with deficient immunological response: an Italian randomized clinical trial." PLoS One 8(11): e80157.

(Continued)

*Primary Examiner* — Janet L Andres
*Assistant Examiner* — Stuart W Snyder
(74) *Attorney, Agent, or Firm* — Westman, Champlin & Koehler, P.A.; Z. Peter Sawicki; Visala C. Goswitz

(57) ABSTRACT

Methods of treating a patient with human immunodeficiency virus are disclosed. The method includes a providing intradermal and intravenous doses of a aTh1 composition that can increase the CD4+ cells in a patient that are resistant to HIV. The description includes a method for viral load reduction and a viral purge method. The regimen leads to a spike in the viral load and a then a return to baseline or lower levels of the virus and can lead to reduction and/or elimination of the latent viral reservoirs. Kits configured to provide intradermal doses and intravenous doses according to the regimen are also included.

9 Claims, No Drawings

(56) References Cited

OTHER PUBLICATIONS

Scherer, E., D. Douek, et al. (2008). "25 years of HIV research on virology, virus restriction, immunopathogenesis, genes and vaccines." Clin Exp Immunol 154(1): 6-14.
Schwitalle, Y., M. Linnebacher, et al. (2004). "Immunogenic peptides generated by frameshift mutations in DNA mismatch repair-deficient cancer cells." Cancer Immun 4: 14.
Seelamgari, A., A. Maddukuri, et al. (2004). "Role of viral regulatory and accessory proteins in HIV-1 replication." Front Biosci 9: 2388-2413.
Sereti, I., K. B. Anthony, et al. (2004). "IL-2-induced CD4+ T-cell expansion in HIV-infected patients is associated with long-term decreases in T-cell proliferation." Blood 104(3): 775-780.
Sierra, S., B. Kupfer, et al. (2005). "Basics of the virology of HIV-1 and its replication." J Clin Virol 34(4): 233-244.
Siliciano, J. D. and R. F. Siliciano (2014). "Recent developments in the search for a cure for HIV-1 infection: targeting the latent reservoir for HIV-1." J Allergy Clin Immunol 134(1): 12-19.
Smalls-Mantey, A., M. Connors, et al. (2013). "Comparative efficiency of HIV-1-infected T cell killing by NK cells, monocytes and neutrophils." PLoS One 8(9): e74858.
Svicher, V., E. Balestra, et al. (2011). "HIV-1 dual/mixed tropic isolates show different genetic and phenotypic characteristics and response to maraviroc in vitro." Antiviral Res 90(1): 42-53.
Teerlink, T., H. Versantvoort, et al. (1987). "Antigenic and immunogenic properties of cyanogen bromide peptides from a serotype 5 gonococcal outer membrane protein I." Antonie Van Leeuwenhoek 53(6): 493-499.
Toma, J., J. M. Whitcomb, et al. (2010). "Dual-tropic HIV type 1 isolates vary dramatically in their utilization of CCR5 and CXCR4 coreceptors." AIDS 24(14): 2181-2186.
Vanham, G., L. Penne, et al. (1999). "Decreased CD40 ligand induction in CD4 T cells and dysregulated IL-12 production during HIV infection." Clin Exp Immunol 117(2): 335-342.
Wattanutchariya, N., V. Sirisanthana, et al. (2013). "Effectiveness and safety of protease inhibitor-based regimens in HIV-infected Thai children failing first-line treatment." HIV Med 14(4): 226-232.
Wodarz, D. (2001). "Helper-dependent vs. helper-independent CTL responses in HIV infection: implications for drug therapy and resistance." J Theor Biol 213(3): 447-459.
Wong, K. L., F. C. Lew, et al. (2008). "CD40L-expressing CD8 T cells prime CD8alpha(+) DC for IL-12p70 production." Eur J Immunol 38(8): 2251-2262.
Yin, Q. Q., Y. M. Shao, et al. (2014). "HIV cure and HIV reservoirs." Biomed Environ Sci 27(6): 478-480.
Young, J. M., R. A. Ffrench, et al. (2001). "In vitro HIV-specific CTL activity from HIV-seropositive individuals is augmented by interleukin-12 (IL-12)." AIDS Res Hum Retroviruses 17(3): 233-242.
Zeng, J., J. Muller-Berghaus, et al. (2006). "Identification of HLA class I dependent immunogenic peptides from clonotypic TCRbeta expressed in cutaneous T-cell lymphoma." Int J Cancer 119(10): 2476-2480.
Zhan, P. and X. Liu (2011). "Novel HIV-1 non-nucleoside reverse transcriptase inhibitors: a patent review (2005-2010)." Expert Opin Ther Pat 21(5): 717-796.
Zimmerli, S. C., A. Harari, et al. (2005). "HIV-1-specific IFN-gamma/IL-2-secreting CD8 T cells support CD4-independent proliferation of HIV-1-specific CD8 T cells." Proc Natl Acad Sci U S A 102(20): 7239-7244.
di Marzio, P., R. Mariani, et al. (2000). "Soluble CD40 ligand induces beta-chemokine production by macrophages and resistance to HIV-1 entry." Cytokine 12(10): 1489-1495. Abstract.
Azizi, A., D. E. Anderson, et al. (2006). "Immunogenicity of a polyvalent HIV-1 candidate vaccine based on fourteen wild type gp120 proteins in golden hamsters." BMC Immunol 7: 25.
Babbitt, B. P., P. M. Allen, et al. (1985). "Binding of immunogenic peptides to Ia histocompatibility molecules." Nature 317(6035): 359-361.
Baker, J. R., Jr. and T. Leigh (1991). "The immunopathogenesis of AIDS." Dermatol Clin 9(3): 403-413. Abstract.
Becker, Y. (2004). "The changes in the T helper 1 (Th1) and T helper 2 (Th2) cytokine balance during HIV-1 infection are indicative of an allergic response to viral proteins that may be reversed by Th2 cytokine inhibitors and immune response modifiers—a review and hypothesis." Virus Genes 28(1): 5-18. Abstract.
Borras-Cuesta, F., A. Petit-Camurdan, et al. (1987). "Engineering of immunogenic peptides by co-linear synthesis of determinants recognized by B and T cells." Eur J Immunol 17(8): 1213-1215. Abstract.
Borrow, P., H. Lewicki, et al. (1997). "Antiviral pressure exerted by HIV-1-specific cytotoxic T lymphocytes (CTLs) during primary infection demonstrated by rapid selection of CTL escape virus." Nat Med 3(2): 205-211. Abstract.
Bradbury, J. (2013). "HIV-1 capsid structure nailed." Lancet Infect Dis 13(7): 575. Abstract.
Brazille, P., N. Dereuddre-Bosquet, et al. (2003). "Decreases in plasma TNF-alpha level and IFN-gamma mRNA level in peripheral blood mononuclear cells (PBMC) and an increase in IL-2 mRNA level in PBMC are associated with effective highly active antiretroviral therapy in HIV-infected patients." Clin Exp Immunol 131(2): 304-311.
Brockman, M. A., D. S. Kwon, et al. (2009). "IL-10 is up-regulated in multiple cell types during viremic HIV infection and reversibly inhibits virus-specific T cells." Blood 114(2): 346-356.
Buseyne, F., G. Janvier, et al. (1994). "Multispecific and heterogeneous recognition of the gag protein by cytotoxic T lymphocytes (CTL) from HIV-infected patients: factors other than the MHC control the epitopic specificities." Clin Exp Immunol 97(3): 353-360.
Buus, S., A. Sette, et al. (1987). "The interaction between protein-derived immunogenic peptides and Ia." Immunol Rev 98: 115-141. First page.
Caldeira Jdo, C., A. Medford, et al. (2010). "Immunogenic display of diverse peptides, including a broadly cross-type neutralizing human papillomavirus L2 epitope, on virus-like particles of the RNA bacteriophage PP7." Vaccine 28(27): 4384-4393.
Carroll, R. G., J. L. Riley, et al. (1997). "Differential regulation of HIV-1 fusion cofactor expression by CD28 costimulation of CD4+ T cells." Science 276(5310): 273-276.
Chen, L., Y. D. Kwon, et al. (2009). "Structural basis of immune evasion at the site of CD4 attachment on HIV-1 gp120." Science 326(5956): 1123-1127.
Chougnet, C., E. Thomas, et al. (1998). "CD40 ligand and IFN-gamma synergistically restore IL-12 production in HIV-infected patients." Eur J Immunol 28(2): 646-656.
Chowers, M., B. S. Gottesman, et al. (2010). "Nucleoside reverse transcriptase inhibitors in combination therapy for HIV patients: systematic review and meta-analysis." Eur J Clin Microbiol Infect Dis 29(7): 779-786. Abstract.
Cohen, J. (2008). "Virology. HIV gets by with a lot of help from human host." Science 319(5860): 143-144. Abstract.
Cohen, M. S., N. Hellmann, et al. (2008). "The spread, treatment, and prevention of HIV-1: evolution of a global pandemic." J Clin Invest 118(4): 1244-1254.
Cohen, O. J., A. Kinter, et al. (1997). "Host factors in the pathogenesis of HIV disease." Immunol Rev 159: 31-48.
Connolly, N., S. Riddler, et al. (2007). "Levels of antigen processing machinery components in dendritic cells generated for vaccination of HIV-1+ subjects." AIDS 21(13): 1683-1692.
Cotter, R. L., J. Zheng, et al. (2001). "Regulation of human immunodeficiency virus type 1 infection, beta-chemokine production, and CCR5 expression in CD40L-stimulated macrophages: immune control of viral entry." J Virol 75(9): 4308-4320.
Cunningham, A. L., A. N. Harman, et al. (2007). "DC-SIGN 'AIDS' HIV immune evasion and infection." Nat Immunol 8 (6): 556-558.
Curiel, T. J., C. Morris, et al. (2004). "Peptides identified through phage display direct immunogenic antigen to dendritic cells." J Immunol 172(12): 7425-7431.
D'Elios, M. and G. Del Prete (1998). "Th1/Th2 balance in human disease." Transplant Proc 30(5): 2373-2377. First Page.

(56) References Cited

OTHER PUBLICATIONS

Deeks, S. (2014). "Towards an HIV cure." J Int AIDS Soc 17(4 Suppl 3): 19479. Abstract.
Diallo, M., Y. Zheng, et al. (2011). "Prospect of IL-2, IL-7, IL-15 and IL-21 for HIV immune-based therapy." Zhong Nan Da Xue Xue Bao Yi Xue Ban 36(11): 1037-1045.
Ding, Y., S. V. Seow, et al. (2009). "Coadministration of the fungal immunomodulatory protein FIP-Fve and a tumour-associated antigen enhanced antitumour immunity." Immunology 128(1 Suppl): e881-894.
Douek, D. C., J. M. Brenchley, et al. (2002). "HIV preferentially infects HIV-specific CD4+ T cells." Nature 417(6884): 95-98.
Dyson, H. J., E. Norrby, et al. (1992). "Immunogenic peptides corresponding to the dominant antigenic region alanine-597 to cysteine-619 in the transmembrane protein of simian immunodeficiency virus have a propensity to fold in aqueous solution." Biochemistry 31(5): 1458-1463. First Page.
Elofsson, M., S. Roy, et al. (1993). "Solid-phase synthesis and conformational studies of glycosylated derivatives of helper-T-cell immunogenic peptides from hen-egg lysozyme." Carbohydr Res 246: 89-103. Abstract.
Fan, Z., X. L. Huang, et al. (1997). "Cultured blood dendritic cells retain HIV-1 antigen-presenting capacity for memory CTL during progressive HIV-1 infection." J Immunol 159(10): 4973-4982. Abstract.
Fanales-Belasio, E., M. Raimondo, et al. (2010). "HIV virology and pathogenetic mechanisms of infection: a brief overview." Ann Ist Super Sanita 46(1): 5-14.
Fauci, A. S. (1996). "Host factors in the pathogenesis of HIV disease." Antibiot Chemother (1971) 48: 4-12.
Feng, Y. M., Y. M. Wan, et al. (2010). "HIV-specific IL-2(+) and/or IFN-gamma(+) CD8(+) T cell responses during chronic HIV-1 infection in former blood donors." Biomed Environ Sci 23(5): 391-401.
Ferrantelli, F., M. T. Maggiorella, et al. (2011). "A combination HIV vaccine based on Tat and Env proteins was immunogenic and protected macaques from mucosal SHIV challenge in a pilot study." Vaccine 29(16): 2918-2932.
Flower, D. R. (2013). "Designing immunogenic peptides." Nat Chem Biol 9(12): 749-753. Abstract.
Forster, M. J. and S. G. Rijpkema (2000). "Selection of putative immunogenic peptides by molecular modelling of the urease of Helicobacter pylori." Dev Biol (Basel) 103: 75-79. Abstract.
Franco, D., W. Liu, et al. (2011). "CD40L-containing virus-like particle as a candidate HIV-1 vaccine targeting dendritic cells." J Acquir Immune Defic Syndr 56(5): 393-400.
Frankel, D. H. (1996). "Structure of HIV p24 capsid protein revealed." Lancet 348(9021): 184. Summary.
Garcia, F., J. C. Bernaldo de Quiros, et al. (2011). "Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: A phase I clinical trial (RISVAC02)." Vaccine 29(46): 8309-8316.
Gazarian, K., T. Gazarian, et al. (2011). "Immunogenic peptides from phage display libraries with potential of protecting mice against the Pseudorabies virus." Vet Microbiol 154(1-2): 29-36. Abstract.
Geretti, A. M., D. Armenia, et al. (2012). "Emerging patterns and implications of HIV-1 integrase inhibitor resistance." Curr Opin Infect Dis 25(6): 677-686.
Gu, H., H. Zhu, et al. (2009). "Use of in vivo-induced antigen technology (IVIAT) for the identification of Streptococcus suis serotype 2 in vivo-induced bacterial protein antigens." BMC Microbiol 9: 201.
Guttman, M. and K. K. Lee (2013). "A functional interaction between gp41 and gp120 is observed for monomeric but not oligomeric, uncleaved HIV-1 Env gp140." J Virol 87(21): 11462-11475.

Haas, G., A. Samri, et al. (1998). "Cytotoxic T-cell responses to HIV-1 reverse transcriptase, integrase and protease." AIDS 12(12): 1427-1436.
Har-Noy, M. and S. Slavin (2008). "The anti-tumor effect of allogeneic bone marrow/stem cell transplant without graft vs. host disease toxicity and without a matched donor requirement?" Med Hypotheses 70(6): 1186-1192.
Har-Noy, M., M. Zeira, et al. (2009). "Allogeneic CD3/CD28 cross-linked Th1 memory cells provide potent adjuvant effects for active immunotherapy of leukemia/lymphoma." Leuk Res 33(4): 525-538.
Har-Noy, M., M. Zeira, et al. (2008). "Completely mismatched allogeneic CD3/CD28 cross-linked Th1 memory cells elicit anti-leukemia effects in unconditioned hosts without GVHD toxicity." Leuk Res 32(12): 1903-1913.
Helbert, M. R., J. Walter, et al. (1997). "HIV infection of CD45RA+ and CD45RO+ CD4+ T cells." Clin Exp Immunol 107(2): 300-305.
Hinuma, S., M. Hazama, et al. (1991). "A novel strategy for converting recombinant viral protein into high immunogenic antigen." FEBS Lett 288(1-2): 138-142.
Hoxie, J. A., C. C. LaBranche, et al. (1998). "CD4-independent utilization of the CXCR4 chemokine receptor by HIV-1 and HIV-2." J Reprod Immunol 41(1-2): 197-211. Abstract.
Huang, X. L., Z. Fan, et al. (2008). "Maturation of dendritic cells for enhanced activation of anti-HIV-1 CD8(+) T cell immunity." J Leukoc Biol 83(6): 1530-1540.
Hutter, G., D. Nowak, et al. (2009). "Long-term control of HIV by CCR5 Delta32/Delta32 stem-cell transplantation." N Engl J Med 360(7): 692-698.
Ishida, Y., Y. Abe, et al. (2006). "Identification of human T-cell epitopes and highly immunogenic analog peptides on the non-typeable Haemophilus influenzae P6 outer membrane protein." Clin Immunol 121(1): 90-99.
Jaeger, E., H. Bernhard, et al. (1996). "Generation of cytotoxic T-cell responses with synthetic melanoma-associated peptides in vivo: implications for tumor vaccines with melanoma-associated antigens." Int J Cancer 66(2): 162-169.
Jia, M., K. Hong, et al. (2012). "Preferential CTL targeting of Gag is associated with relative viral control in long-term surviving HIV-1 infected former plasma donors from China." Cell Res 22(5): 903-914.
Kanduc, D. (2005). "Peptimmunology: immunogenic peptides and sequence redundancy." Curr Drug Discov Technol 2 (4): 239-244. Abstract.
Kaul, R., K. S. MacDonald, et al. (2010). "HIV viral set point and host immune control in individuals with HIV-specific CD8+ T-cell responses prior to HIV acquisition." AIDS 24(10): 1449-1454.
Kidd, P. (2003). "Th1/Th2 balance: the hypothesis, its limitations, and implications for health and disease." Altern Med Rev 8(3): 223-246.
Kirchhoff, F. (2010). "Immune evasion and counteraction of restriction factors by HIV-1 and other primate lentiviruses." Cell Host Microbe 8(1): 55-67.
Klein, B. S., P. M. Sonde!, et al. (1992). "WI-1, a novel 120-kilodalton surface protein on Blastomyces dermatitidis yeast cells, is a target antigen of cell-mediated immunity in human blastomycosis." Infect Immun 60(10): 4291-4300.
Klein, S. A., J. M. Dobmeyer, et al. (1997). "Demonstration of the Th1 to Th2 cytokine shift during the course of HIV-1 infection using cytoplasmic cytokine detection on single cell level by flow cytometry." AIDS 11(9): 1111-1118.
Kornbluth, R. S. (2000). "The emerging role of CD40 ligand in HIV infection." J Leukoc Biol 68(3): 373-382.
Kornbluth, R. S., K. Kee, et al. (1998). "CD40 ligand (CD154) stimulation of macrophages to produce HIV-1-suppressive beta-chemokines." Proc Natl Acad Sci U S A 95(9): 5205-5210.
Korthals Altes, H., R. M. Ribeiro, et al. (2003). "The race between initial T-helper expansion and virus growth upon HIV infection influences polyclonality of the response and viral set-point." Proc Biol Sci 270(1522): 1349-1358.
Kwong, P. D., M. L. Doyle, et al. (2002). "HIV-1 evades antibody-mediated neutralization through conformational masking of receptor-binding sites." Nature 420(6916): 678-682. Abstract.

(56) References Cited

OTHER PUBLICATIONS

Lagier, J. C. and D. Raoult (2014). "Immune reconstitution inflammatory syndrome associated with bacterial infections." Expert Opin Drug Saf 13(3): 341-350. Abstract.
Leghmari, K., Y. Bennasser, et al. (2008). "HIV-1 Tat protein induces IL-10 production in monocytes by classical and alternative NF-kappaB pathways." Eur J Cell Biol 87(12): 947-962. Abstract.
Leone, A., L. J. Picker, et al. (2009). "IL-2, IL-7 and IL-15 as immuno-modulators during SIV/HIV vaccination and treatment." Curr HIV Res 7(1): 83-90. Abstract.
Li, F., D. Song, et al. (2013). "Delayed-type hypersensitivity (DTH) immune response related with EBV-DNA in nasopharyngeal carcinoma treated with autologous dendritic cell vaccination after radiotherapy." J Immunother 36(3): 208-214.
Li, M. and R. Craigie (2006). "Virology: HIV goes nuclear." Nature 441(7093): 581-582. Abstract.
Liu, J., Q. Yu, et al. (2008). "CD40L expressed from the canarypox vector, ALVAC, can boost immunogenicity of HIV-1 canarypox vaccine in mice and enhance the in vitro expansion of viral specific CD8+ T cell memory responses from HIV-1-infected and HIV-1-uninfected individuals." Vaccine 26(32): 4062-4072.
Loftin, L. M., M. Kienzle, et al. (2011). "R5X4 HIV-1 coreceptor use in primary target cells: implications for coreceptor entry blocking strategies." J Trans! Med 9 Suppl 1: S3.
Longenecker, B. M., M. Reddish, et al. (1993). "Immune responses of mice and human breast cancer patients following immunization with synthetic sialyl-Tn conjugated to KLH plus detox adjuvant." Ann N Y Acad Sci 690: 276-291. Abstract.
Malim, M. H. and M. Emerman (2008). "HIV-1 accessory proteins—ensuring viral survival in a hostile environment." Cell Host Microbe 3(6): 388-398.
Martin, N. and Q. Sattentau (2009). "Cell-to-cell HIV-1 spread and its implications for immune evasion." Curr Opin HIV AIDS 4(2): 143-149.
McAdam, S., P. Klenerman, et al. (1995). "Immunogenic HIV variant peptides that bind to HLA-B8 can fail to stimulate T lymphocyte responses." J Immunol 155(5): 2729-2736. Abstract cytotoxic.
McDyer, J. F., M. Dybul, et al. (1999). "Differential effects of CD40 ligand/trimer stimulation on the ability of dendritic cells to replicate and transmit HIV infection: evidence for CC-chemokine-dependent and -independent mechanisms." J Immunol 162(6): 3711-3717.
Mecheri, S., G. Dannecker, et al. (1990). "Immunogenic peptides require an undisturbed phospholipid cell membrane environment and must be amphipathic to immobilize la on B cells." J Immunol 144(4): 1369-1374. Abstract.
Moore, J. P., A. Trkola, et al. (1997). "Co-receptors for HIV-1 entry." Curr Opin Immunol 9(4): 551-562. Abstract.
Mosmann, T. R. and R. L. Coffman (1989). "TH1 and TH2 cells: different patterns of lymphokine secretion lead to different functional properties." Annu Rev Immunol 7: 145-173.
Mosmann, T. R. and S. Sad (1996). "The expanding universe of T-cell subsets: Th1, Th2 and more." Immunol Today 17(3): 138-146.
Mothe, B., a. Llano, et al. (2012). "CTL responses of high functional avidity and broad variant cross-reactivity are associated with HIV control." PLoS One 7(1): e29717.
Natarajan, V., R. A. Lempicki, et al. (2002). "Increased peripheral expansion of naive CD4+ T cells in vivo after IL-2 treatment of patients with HIV infection." Proc Natl Acad Sci U S A 99(16): 10712-10717.
Nurutdinova, D. and E. T. Overton (2009). "A review of nucleoside reverse transcriptase inhibitor use to prevent perinatal transmission of HIV." Expert Opin Drug Saf 8(6): 683-694. Abstract.
Okello, M., M. Nishonov, et al. (2013). "Approaches to the synthesis of a novel, anti-HIV active integrase inhibitor." Org Biomol Chem 11(45): 7852-7858.
Pancera, M., S. Majeed, et al. (2010). "Structure of HIV-1 gp120 with gp41-interactive region reveals layered envelope architecture and basis of conformational mobility." Proc Natl Acad Sci U S A 107(3): 1166-1171.
Papagno, L., G. Alter, et al. (2011). "Comprehensive analysis of virus-specific T-cells provides clues for the failure of therapeutic immunization with ALVAC-HIV vaccine." AIDS 25(1): 27-36.
Peabody, D. S., B. Manifold-Wheeler, et al. (2008). "Immunogenic display of diverse peptides on virus-like particles of RNA phage MS2." J Mol Biol 380(1): 252-263.
Petrov, R. V., M. R. Khaitov, et al. (2008). "Immunogenic properties of recombinant and synthetic peptides of Human papillomavirus." Dokl Biochem Biophys 421: 185-190.
Pido-Lopez, J., Y. Wang, et al. (2009). "The effect of allogeneic in vitro stimulation and in vivo immunization on memory CD4(+) T-cell APOBEC3G expression and HIV-1 infectivity." Eur J Immunol 39(7): 1956-1965.
Piguet, V. and D. Trono (2001). "Living in oblivion: HIV immune evasion." Semin Immunol 13(1): 51-57. Abstract.
Poli, G. (2013). "Cell-to-cell vs. cell-free HIV-1 transmission from macrophages to CD4+ T lymphocytes: lessons from the virology textbook." AIDS 27(14): 2307-2308.
Pomerantz, R. J. (2002). "Clinical HIV-1 virology." Clin Lab Med 22(3): xi-xiii.
Riley, J. L., R. G. Carroll, et al. (1997). "Intrinsic resistance to T cell infection with HIV type 1 induced by CD28 costimulation." J Immunol 158(11): 5545-5553.
Riley, J. L., B. L. Levine, et al. (1998). "Naive and memory CD4 T cells differ in their susceptibilities to human immunodeficiency virus type 1 infection following CD28 costimulation: implicatip6s for transmission and pathogenesis." J Virol 72(10): 8273-8280.
Romagnani, S., G. Del Prete, et al. (1994). "Role of TH1/TH2 cytokines in HIV infection." Immunol Rev 140: 73-92.
Rothbard, J. B. and R. Busch (1990). "Interactions between immunogenic peptides and HLA-DR molecules." Immunol Res 9(3): 178-189.
Search Report issued for corresponding Singapore patent application No. 11201605440T, dated Mar. 20, 2017.
Office Action issued for related Japanese patent application No. 2016-545336, dated Oct. 10, 2018.
Extended European Search Report issued for related European application No. 15735377.2 dated Aug. 23, 2017.

* cited by examiner

TREATMENT OF HUMAN IMMUNODEFICIENCY VIRUS/ACQUIRED IMMUNODEFICIENCY SYNDROME

CROSS-REFERENCE TO RELATED APPLICATION

The present application is based on and claims the benefit of U.S. provisional patent application Ser. No. 61/924,936, filed Jan. 8, 2014, the content of which is hereby incorporated by reference in its entirety.

FIELD

This disclosure relates to treatment of anti-retroviral therapy and more particularly relates to immunotherapy treatment of HIV/AIDS.

BACKGROUND

AIDS was first reported in the United States in 1981 and has since become a major worldwide pandemic. AIDS is caused by the human immunodeficiency virus, or HIV. Today more than 30 million people living throughout the world are infected by the virus (Cohen, Hellmann et al. 2008). HIV progressively destroys the body's ability to fight infections and other diseases by killing or damaging cells of the body's immune system, specifically eliminating immune cells that express the CD4 molecule, such as CD4+ helper T-lymphocytes (leading to an inverted CD4/CD8 T-cells ratio) and cells of the monocyte/macrophage lineage (Fauci 1996).

CD4 T-cells mature into two polarized functional types, called Th1 and Th2 (Mosmann and Coffman 1989; Mosmann and Sad 1996). Th1 CD4+ cells are responsible for mediating cellular immunity and Th2 CD4+ cells are responsible for mediating humoral immunity (D'Elios and Del Prete 1998). HIV infection causes a gradual loss of the Th1 subset resulting in an inverted Th1/Th2 ratio (Becker 2004) and loss of cellular immunity. The loss of Th1 immunity and switch to Th2-dominated immunity in HIV patients has been correlated with profound immunosuppression and the progression from HIV positive status to AIDS (Klein, Dobmeyer et al. 1997). One of the leading causes of death of patients with AIDS is opportunistic infections due to the suppression of the cellular immune system (Baker and Leigh 1991).

HIV has multiple strategies for immune evasion. These strategies include mutational escape, latency, masking of antibody-binding sites on the viral envelope, down-modulation of the class I major histocompatibility complex (MHC-I), up-regulation of the Fas ligand on the surface of infected cells (Piguet and Trono 2001) and inducing the production of IL-10 (Leghmari, Bennasser et al. 2008; Brockman, Kwon et al. 2009). In addition, Some viral genes such as vif, vpr, vpu, and nef genes translate proteins that act to suppress anti-viral immune responses (Kirchhoff 2010). These viral escape mechanisms make the virus elusive for control using immunological methods (Migueles, Tilton et al. 2006; Bansal, Yue et al. 2007; Feinberg and Ahmed 2012; Teshome and Assefa 2014).

HIV virology has been intensively studied and the viral structure and life cycle of HIV has been described (Pomerantz 2002; Sierra, Kupfer et al. 2005; Li and Craigie 2006; Cohen 2008; Scherer, Douek et al. 2008; Fanales-Belasio, Raimondo et al. 2010). A single HIV particle is called a virion. The virion is shaped like a spiked sphere. The central core of the sphere is called the capsid. The caspid contains two single strands of HIV RNA called viral RNA. When viral RNA is detected in the serum, the quantity of viral RNA is called the viral load. The viral RNA codes for three enzymes important to the virus's life cycle called reverse transcriptase, integrase, and protease. These enzymes are foreign to human immune system and are capable of being recognized by CD8+ CTL killer cells (Haas, Samri et al. 1998). In this manner, cells that express these viral enzymes are targets for immune elimination. However, the viral RNA also contains instructions for production of viral accessory proteins that serve to assist the virus to evade immune elimination (Seelamgari, Maddukuri et al. 2004; Malim and Emerman 2008).

Surrounding the core is a protective lipid (fat) bilayer which forms a shell around the capsid (Frankel 1996; Bradbury 2013). This shell is called the viral envelope. Embedded within the viral envelope is a HIV protein called env. The env protein is made up of two glycoproteins, gp120 and gp41, that protrude from the virion forming the spikes. The cap of the spike is gp120 and the stem is gp41. For HIV to enter a host cell, it must first use gp120 to attach to a CD4 receptor (Pancera, Majeed et al. 2010; Guttman and Lee 2013).

After gp120 successfully attaches to a CD4 cell, the molecule can change shape to avoid recognition by neutralizing antibodies, a process known as conformational masking (Kwong, Doyle et al. 2002). The conformational change in gp120 allows it to bind to a second receptor on the CD4 cell surface called a chemokine receptor.

The chemokine receptor on the CD4 cells surface used as a co-receptor for the HIV virion is either CCR5 or CXCR4 (Moore, Trkola et al. 1997). The viral preference for using one chemokine co-receptor versus another is called 'viral tropism'. Chemokine receptor 5 (CCR5), is used by macrophage-tropic (M-tropic) HIV to bind to a cell (Cohen, Kinter et al. 1997). About 90% of all HIV infections involve the M-tropic HIV strain. CXCR4, also called fusin, is a chemokine receptor used by T-tropic HIV (ones that preferentially infect CD4 T-cells) to attach to the host cell (Hoxie, LaBranche et al. 1998). Another co-receptor called DC-SIGN is expressed on dendritic cells and also binds gp120 in order to facilitate viral infection of these important cells involved in cellular immunity (Cunningham, Harman et al. 2007). Viral infected macrophages can interact with CD4 T-cells and pass the virus through cell-to-cell contract (Martin and Sattentau 2009; Poli 2013). In addition, HIV can induce T-cells to form syncytium to facilitate cell-to-cell viral transfer (Emilie, Maillot et al. 1990; Kozal, Ramachandran et al. 1994; Margolis, Glushakova et al. 1995).

Transmission of HIV results in the establishment of a new infection, starting from even a single virion particle. HIV virons are replicated within host infected cells and released into the plasma which causes viremia and persistent infection of immune cells in all of the lymphoid tissues in the body. HIV preferentially infects T cells with high levels of CD4 surface expression and those subsets of T cells that co-express CCR5. The subset of memory T-cells are a preferred target (Helbert, Walter et al. 1997), particularly HIV-specific memory T cells (Douek, Brenchley et al. 2002) and Th2/Th0 cells (Maggi, Mazzetti et al. 1994).

With the onset of immunodeficiency, the virus evolves to infect new cell types. This correlates with a tropism change involves switching from preference for CCR5 co-receptor to the alternative CXCR4 co-receptors. This switch corresponds with an expansion of infected cells to include naive CD4+ T cells in addition to the preferred memory cells.

Similarly, the virus evolves the ability to enter cells with low levels of CD4 on the surface and this potentiates the ability to infect monocyte/macrophages. Naïve cells are found almost exclusively in the secondary lymphoid organs, while memory cells and macrophages have a much wider tissue distribution, including the brain, tissue and organ systems. Infection of naïve cells and macrophages establishes pools of viral infected cells throughout the body and in locations that are difficult to target with drugs or immunotherapy.

M-tropic and T-tropic strains of HIV can also coexist in the body, further complicating the ability to target elimination of the virus. At some point in infection, gp120 is able to attach to either CCR5 or CXCR4. A HIV virion with this property is called a dual tropic virus or R5X4 HIV (Toma, Whitcomb et al. 2010; Loftin, Kienzle et al. 2011; Svicher, Balestra et al. 2011). HIV that can utilize the CXCR4 receptor on both macrophages and T-cells is also termed dual-tropic X4 HIV (Huang, Eshleman et al. 2009; Gouwy, Struyf et al. 2011; Xiang, Pacheco et al. 2013). Mixed tropism results when an individual has two virus populations; one using CCR5 and the other CXCR4 to bind to the CD4 T-cell. Since the virological behavior of T-tropic and M-tropic viruses vary, mixed tropism creates a difficult problem for drug design.

Once the HIV envelope has attached to the CD4 molecule and is bound to a co-receptor, the HIV envelope utilizes a structural change in the gp41 envelope protein to fuse with the cell membrane and evade neutralizing antibodies (Chen, Kwon et al. 2009). The HIV virion is then able to penetrate the target cell membrane.

Once within a host cell, the viral enzyme reverse transcriptase converts the viral RNA to viral DNA. Reverse transcriptase inhibitors are developed as an anti-HIV therapy (Nurutdinova and Overton 2009; Chowers, Gottesman et al. 2010; Zhan and Liu 2011). Once the viral RNA is transcribed to DNA, the DNA is then able to enter the nucleus of the host cell. Using another viral enzyme called integrase, the viral DNA is able to integrate into the host cell's chromosomal DNA. Integrase inhibition is another target of anti-viral drug development (Geretti, Armenia et al. 2012; Okello, Nishonov et al. 2013). The integrated viral DNA is called provirus and is replicated along with the host chromosome when the host cell divides. The integration of provirus into the host DNA provides the latency that enables the virus to effectively evade host immune responses.

When the host cell is activated to divide, production of viral proteins and viral RNA takes place as the provirus is transcribed along with the host DNA. Viral proteins are then assembled using the host cell's protein-making machinery. The virus's protease enzyme allows for the processing of newly translated viral polypeptides into the proteins which constitute the virus. These various proteins are then ultimately assembled into viral particles. Protease inhibitors are another class of anti-viral drugs for treatment of HIV infection (Wattanutchariya, Sirisanthana et al. 2013). The assembled virus uses the nuclear capsid protein called gag to interact with host protein machinery to cause the budding of the virus and release of whole virus from the host cell (Dussupt, Javid et al. 2009). Alternatively, the budding HIV can transfer directly from cell-to-cell interaction (Fais, Capobianchi et al. 1995). Many viral particles can bud from of a single cell over the course of time, eventually lysing the cell membrane killing the cell.

Cells actively producing virus are vulnerable to attack by CD8 cells (cytotoxic T-lymphocytes or CTLs). CTL cells require help from Th1 CD4 cells to kill cells that are producing virus (Wodarz 2001). In HIV infection, the viral load can be kept in a steady state with the rate of immune-mediated destruction of viral producing cells balanced with the rate of release of viral particles from infected cells. In this steady state, the viral load is maintained at a set point level (Korthals Altes, Ribeiro et al. 2003; Kaul, MacDonald et al. 2010). When CD4 counts drop sufficient to lose this helper function for CTL, the set point control is lost and the viral load climbs. Eventually this leads to a fall in CD4 counts, loss of cellular immunity and eventually leading to AIDS. An HIV infection can be in such a steady state for eight to ten years before the clinical syndrome of AIDS occurs (Jurriaans and Goudsmit 1996; Callaway and Perelson 2002; Maenetje, Riou et al. 2010).

The most obvious laboratory observation in HIV infection is a decline in the number of CD4+ T-cells found in the blood and a decline in the CD4/CD8 ratio. Increase in viral load (viral RNA) can be detected by sensitive PCR tests.

Highly active antiretroviral therapy (HAART) for the chronic suppression of HIV replication has been the major accomplishment in HIV/AIDS medicine. HAART cocktails contain drugs with different mechanisms of action designed to block the natural virus life cycle at different points. For example, HAART can contain reverse transcriptase, integrase, protease and binding (Carter 2003; Laurence 2004; 2007) inhibitors. Many patients are now in their second decade of treatment, with levels of plasma HIV RNA (viral load) below the limits of detection of clinical assays (e.g., <50 copies/ml). New HAART drugs are being developed to interfere with the viral life cycle. For example, since CCR5 has been identified as a major HIV co-receptor this has lead to the development of drugs that target the virus-CCR5 interaction, including the first-in-class approved drug, Maraviroc (Rusconi, Vitiello et al. 2013).

Since HAART is not able to completely eliminate the virus, life-long antiviral therapy is needed to control HIV infection. Such therapy is expensive and prone to drug resistance, cumulative side effects and unknown effects of long-term treatment. HAART has several long-term side effects including kidney, liver, and pancreatic problems; and changes in fat metabolism, which result in elevated cholesterol and triglyceride levels and an increased risk for strokes and heart attacks (Carter 2003; Laurence 2004; 2007). In addition, some viruses have evolved resistance to HAART (Fumero and Podzamczer 2003; Tebit, Sangare et al. 2008; Loulergue, Delaugerre et al. 2011).

HIV infection persists in spite of efficacious HAART therapies as evidenced by rapid rebound of viremia upon cessation of HAART therapy most often within 3-10 days (Neumann, Tubiana et al. 1999; Van Gulck, Heyndrickx et al. 2011). This phenomenon is thought to be due to the early establishment of a stable reservoir of latently infected cells with integrated viral DNA that seeds the production of virions after HAART cessation.

The goal of HAART therapy in HIV-infected patients is to reduce plasma HIV viral load (HIV RNA) to undetectable levels and to increase the CD4 cell count. Achievement of this goal reduces the rate of disease progression and death. However, some patients experience isolated episodes of transiently detectable HIV RNA or viral rebound (Staszewski, Miller et al. 1998; Butler, Gavin et al. 2014). The causes of viral rebound are still unclear. Rates of viral rebound of 25-53% have been reported among patients on HAART who have achieved undetectable HIV RNA. Viral rebound that then persists as a low level viremia (set point level) may lead to genetic mutations in the virus leading to drug resistance.

Patients with persistent low-level viremia have a higher rate of virological failure. Persistent low-level viremia is defined as plasma HIV RNA levels in the range of 51-1000 copies/mL for at least 3 months and on at least two consecutive clinic visits. Virological failure is defined as two consecutive plasma HIV RNA levels >1000 copies/mL.

After HAART initiation, most patients experience improved immune function and maintain viral suppression; however, there remains a subset of patients who have suboptimal immunologic responses—defined as the failure to achieve and maintain an adequate CD4 response despite use of HAART therapy. Patients with inadequate CD4 counts on HAART therapy are said to have immunological failure. Adequate CD4 counts are generally defined as >500 cells/mm$^3$ over a specific period of time (e.g., 4 to 7 years). Immunological failure increases the risk of AIDS- and non-AIDS-related morbidity and mortality. For example, a low CD4 count of <500 is associated with an increased risk in cardiovascular, hepatic, and renal disease and cancer.

Cytotoxic T lymphocyte (CTL) and Natural Killer (NK) cell responses are important to the initial decrease in HIV viral load seen in the first several months after acute infection (Borrow, Lewicki et al. 1997; Fan, Huang et al. 1997; Smalls-Mantey, Connors et al. 2013). These beneficial cellular immune responses diminish with disease progression and cannot be recovered with antiretroviral therapy alone. CTL responses generally require CD4 cell help to be effective (Wodarz 2001).

Recent studies suggest a therapeutic vaccine may help to restore cellular immunity and CTL and NK responses to the virus. Therapeutic HIV vaccines are designed to control HIV infection by boosting the body's natural immune response. HIV-specific T-cell-based vaccines have been extensively studied in both prevention and therapeutic settings, with most studies failing to show benefit, and some suggesting harm (Papagno, Alter et al. 2011). There are currently no FDA-approved therapeutic HIV vaccines.

So far it has been impossible to cure HIV despite long-term viral suppression on HAART. The rapid rebound despite powerful viral suppression and blockage of viral entry is thought to be due to the reservoirs of latently infected cells unaffected by viral suppression and unable to be targeted for immune elimination, also the continuous sub-clinical viral production from some cells in lymph nodes and tissues and the ability of the virus to spread through cell-to-cell contact as an alternative to entry pathway all serve to maintain viral persistence.

While there are descriptions of some patients that can remain with undetectable virus without HAART, these so called "secondary controllers" are infected with less infectious types of HIV (Lobritz, Lassen et al. 2011; Van Gulck, Bracke et al. 2012). For the majority of patients, HAART is a lifetime requirement for disease control.

The only report of long-term viral suppression after cessation of HAART therapy is the so called "Berlin Patient". The Berlin Patient received an allogeneic stem cell transplant for treatment of his leukemia. The donor had a special genetic characteristic (two copies of the recessive CCR5Δ32 allele) which results in the inability to express the CCR5 receptor on the surface of CD4 cells. Thus the donor cells for the transplant were resistant to viral entry. After transplant, the patient was able to stop all HAART antiretroviral therapy and remained with undetectable viral load for 3½ years after the transplant (Hutter, Nowak et al. 2009).

It is possible that innate or acquired immunity delivered by the donor immune system may have contributed to the elimination of cells with active HIV replication. The patient experienced graft versus host disease (GVHD), and it is possible that an allogeneic immune response directed against host lymphocytes had a purging effect on the latent HIV reservoir in lymphocytes.

Allogeneic stem cell transplant is a highly toxic procedure with high treatment related mortality and morbidity. The high toxicity is related to the need for chemotherapy conditioning regimes and to the often lethal GVHD side-effect. The toxicity of GVHD limits the clinical use of allogeneic transplant procedures to terminally-ill patients without other treatment options. However, in HIV+ patients that are stable on HAART medication, it is not clinically feasible to treat with allogeneic stem cell transplant.

Further, allogeneic transplant requires HLA tissue matched donors. Only ⅓ of individuals have a related HLA-matched donor and fewer are able to find an unrelated HLA matched donor. Moreover, even if a matched donor can be identified, the donor must be homozygous for the CCR5Δ32 mutation, which is an extremely rare genetic phenotype (Jiang, Wang et al. 1999; Williamson, Loubser et al. 2000). Thus the lack of suitable donors and the toxicity of allogeneic transplant procedures makes it impossible to translate data from the Berlin patient to benefit the majority of HIV infected patients.

Accordingly, additional non-toxic therapies are needed in order to exploit the mechanisms that enabled the Berlin Patient to enjoy long-term HAART cessation. In addition, treatment options for virologic failure and immunological failure while on HAART treatment are urgently needed.

SUMMARY

The present description relates to an immunotherapy drug and a therapeutic vaccine composition and methods of use for treating patients with HIV infection that experience virological and/or immunological failure while on HAART medication. In addition, the present description describes a method for purging latent viral pools in HIV patients to levels sufficient to enable extended holiday from the requirement for daily HAART medication.

The compositions of the present description include a combination of living cells, or components thereof, containing at least one highly immunogenic antigen, a molecule that binds surface CD40 receptors to deliver cellular activation signals and one or more inflammatory type 1 cytokines and/or chemokines delivered together or separately in time (hereinafter referred to as "aTh1"). The aTh1 composition may also include at least one anti-retroviral drug. The aTh1 composition that includes anti-retroviral drug may be referred to herein as the AVI composition. The aTh1 composition and anti-viral drugs can be delivered by different routes but the effects of both must be concurrent. The components of the aTh1 composition can be combined in a solution or attached to a surface, such as a biodegradable support, for administration. An exemplary aTh1 composition is known as "AlloStim™" and can be obtained from Immunovative Therapies, Ltd.

The present description includes a method for enhancing CD4+ T-cells in the patient. This CD4 Enhancement Method" includes using the aTh1 composition for increasing the titer of circulating CD4+ Th1 cells in HIV patients, including CD4+ cells that are resistant to HIV infection due to having a memory phenotype and down-regulation of surface CCR5 expression or blocking of CCR5 due to production of chemokine agonists or both. This method can be used concurrently with HAART in HIV patients experiencing immunological failure.

The present description also includes a therapeutic vaccine method. The method includes using aTh1 composition as an adjuvant together with a source of HIV antigen forming a therapeutic vaccine that results in increased titer of HIV-specific T-cells and immune control of the virus. This method can be used as a therapeutic vaccine in HIV patients, including patients on HAART medication experiencing virological failure.

The present description also includes a viral purge method. This method includes using the AVI composition for activating cells latently infected with HIV genetic material so that they produce viral particles and thus become targets for immune-mediated elimination. The anti-viral medication in the AVI composition prevents the awakened latent virus pool to overwhelm and destroy the remaining CD4 cells. This method can be used to decrease or eliminate the latent viral pool. Purging of the latent viral pool is a required step for an eventual cure.

In another aspect of the description, a HIV treatment method is described which combines the CD4 Enhancement method with the Viral Purge method ("HAART Holiday Method"). The HAART Holiday Method can also be combined with the Therapeutic Vaccine Method. The HAART Holiday Method provides HIV patients with an extended holiday from the daily requirement for HAART medications. Such a holiday is preferably longer than 30 days, more preferably for at least 90 days and most preferably for more than a year.

In one aspect, the present description includes a method of treating a patient with HIV. The method includes increasing the titer of circulating CD4+ Th1 memory cells that are resistant to HIV infection by administering at least one intradermal dose of aTh1 composition to the patient wherein the patient is infected with HIV. The method further includes expanding and activating the CD4+ Th1 memory cells in the patient by administering at least one intravenous dose of the aTh1 composition. The method may also includes increasing the titer by administering at least two intradermal doses of aTh1 composition, wherein both of the doses are at the same location and the interval between the intradermal doses is between about 3 days and about a week. The method may also include an additional two intradermal doses of the aTh1 composition at a location different than the location of the first two intradermal doses. The method may also include wherein the patient is concurrently treated with highly active antiretroviral therapy (HAART).

In another aspect, the present description also includes a method of reducing the viral load in a patient with HIV. The method includes administering at least one dose of a aTh1 composition and at least one dose of one or more HIV-antigens, wherein the titer of circulating CD4+ Th1 memory cells that are resistant to HIV infection are increased in the patient and the viral load is decreased in the patient. The method may include wherein the aTh1 composition and the HIV-antigens are administered separately aTh1 composition and the one or more HIV-antigens are administered intradermally.

In yet another aspect, the present description also includes a method of reducing or eliminating HIV-virus from a patient. The method includes escalating intravenous doses of a aTh1 composition to a patient wherein the patient is concurrently treated with HAART. The method may also include a step wherein the HAART is halted and the patient is monitored for CD4+ cells and the viral load and wherein HAART is reinstated if a viral spike is detected in the patient.

In a further aspect, the present description includes a kit comprising components of a therapeutic HIV vaccine wherein the kit comprises intradermal doses of a aTh1 composition, intravenous doses of a aTh1 composition and one or more HIV-antigens. The kit may further include components of HAART.

In yet a further aspect, the present description includes a composition including a aTh1 composition comprising an alloantigen, a molecule that interacts with CD40 surface receptor and Type I cytokines and at least one or more HIV-antigens.

In another further aspect, the present description includes a an AVI composition that includes a aTh1 composition comprising an alloantigen, a molecule that interacts with CD40 surface receptor and Type I cytokines and at least one or more anti-retroviral drugs. The composition may also include one or more HIV-antigens.

DETAILED DESCRIPTION OF ILLUSTRATIVE EMBODIMENTS

This present description includes compositions for patients infected with retroviruses, especially Human Immunodeficiency Virus (HIV). The composition can include the aTh1 composition for eliciting an immunological response by the patient. The present description also includes an anti-viral immunotherapy drug composition (aTh1+ antiviral medication) and methods for using the anti-viral composition for treatment of patients infected with HIV. Methods are described wherein the compositions can be used to: (1) treat immunological failure by increasing the CD4 count (CD4 Enhancement Method); (2) treat virological failure by restoring immune control of viral load (Therapeutic Vaccine Method); and (3) purge virus from the latent viral pool (Viral Purge Method). The combination of all these methods or the combination of the CD4 Enhancement Method and the Viral Purge Method can eliminate the need for daily HAART medication for an extended period of time (HAART Holiday Method).

The anti-viral immunotherapy composition comprising aTh1 and anti-viral medication may be referred to herein as AVI composition.

Patients infected with HIV can be treated with the compositions and methods described herein. The patients may be treated while experiencing immunological or viral failure while on HAART. The patient may be treated with or without simultaneous HAART medication. A biomarker for successful treatment by the composition and methods described herein can be characterized by enhanced serum levels of IL-12 in plasma of the HIV patients. IL-12 can enhance HIV-specific cellular immunity. The methods of the description generally can cause the appearance of IL-12 in the serum by at least 120 days of administering the aTh1 composition, preferably by 90 days, more preferably by 30 days and even more preferably by 7 days. IL-12 can serve as an early biomarker indicating success of the methods in creating anti-HIV immunity.

The aTh1 composition can include i) living cells, or components thereof, containing at least one highly immunogenic antigen, ii) a molecule that delivers a signal through binding to surface CD40 receptor and iii) one or more inflammatory type 1 cytokines and/or chemokines. All of these components of the aTh1 composition can be delivered together or individually at the same time or separately in time.

The highly immunogenic antigen component of the aTh1 composition can be natural, synthetic or recombinant proteins or peptides that have some foreign component that can make them recognizable to the human immune system. The immunogenic antigens can be, for example, allogeneic or xenogenic protein antigens. Self proteins that are altered to be recognized as foreign are also within the scope of the description. The alteration of the self-protein can be by recombinant or chemical means or by mixing the self-protein with an adjuvant. In a preferred embodiment, the highly immunogenic antigen is part of a living cell, preferably an allogeneic living cell, more preferably a living allogeneic immune cell, most preferably an allogeneic living Th1 immune cell. Alloantigens are a preferred highly immunogenic antigen included in the aTh1 composition.

The highly immunogenic antigen(s) of the composition can be capable of being processed by professional antigen presenting cells (APC) for presentation on MHCI and/or MHCII molecules. Examples of highly immunogenic antigens may include also KLH, viral proteins, bacterial protein, yeast proteins, fungal proteins or combinations thereof.

Examples of adjuvants that can increase the immunogenicity of a protein, such as a self protein, include agents which cause immature dendritic cells to mature to IL-12+ DC1 cells. Examples include adjuvant danger signals such as LPS, BCG and Toll-Like receptor agonists (e.g., TLR4 and TLR7). All highly immunogenic peptides and proteins are within the scope of this description.

The aTh1 composition can also include type I cytokines and/or chemokines. Preferred Type 1 cytokines for the aTh1 composition can include interferon-gamma, IL-2, TNF-alpha, TNF-beta, GM-CSF, IL-1, IL-7, IL-15, IL-23 and IL-12 individually or in combinations thereof. Preferred chemokines for the aTh1 composition can include RANTES, MIP-1alpha, MIP-1beta and MCP-1 individually or in combinations thereof. These type I cytokines can either be part of the aTh1 composition or can be induced in the patient by the aTh1 composition.

The aTh1 composition can also include a molecule that delivers a signal through surface CD40 receptor. One preferred molecule in the aTh1 composition that delivers a signal through CD40 is immobilized CD40L (CD154). CD40L (also known as CD154) is a member of the TNF superfamily. CD40L can act as a co-stimulatory molecule that interacts with CD40 expressed on dendritic cells (DC) to support their maturation to a IL-12+ phenotype. CD40L is preferably immobilized by expression on a cell surface so that it provides a positive signal through CD40. Alternatively, an agonist to CD40 can be used to deliver a CD40 signal, such as a fusion protein or an anti-CD40 antibody. The components of the aTh1 composition can be delivered together or separately and in various sequences and at various points in time and are within the scope of this description.

In preferred embodiments, the aTh1 composition can include activated allogeneic CD4+ T-cells, and in more preferred embodiments, allogeneic activated memory CD4+ T-cells with high surface expression of CD40L and which produce interferon-gamma, are used.

IL-12 production and CD40L expression in HIV-infected (HIV+) individuals can be severely impaired. CD40-CD40L interactions are the major mechanism involved in the T cell-dependent activation of antigen-presenting cells (APC), such as DC, to produce IL-12. While CD40, the counter-receptor for CD40L, is expressed on monocytes from HIV+ individuals, IL-12 production can still be suppressed. The appearance of IL-12 in the plasma after administration of the aTh1 composition can indicate successful initiation of the immunological mechanism of the methods.

Different forms of CD40L can also signal through CD40. For example, soluble trimeric CD40L agonist protein (CD40LT), soluble CD40L and CD40L inserted into HIV virus can also provide the same signal and the same effect. All forms of CD40 agonist are within the scope of this description.

In some preferred embodiments, the aTh1 composition can be AlloStim™. AlloStim™ are bioengineered CD4 immune cells derived from the blood of normal donors. AlloStim™ has an activated Th1 memory phenotype: CD4+, CD45RO+, CD62L$^{lo}$, CD40L$^{hi}$, CD25+, interferon-gamma+ and IL-4−. AlloStim™ can be maintained in an activated state by continuous attachment to CD3/CD28-monoclonal antibody-coated microparticles. The key effector molecules of AlloStim™ are the high surface expression of CD40L and the production of high amounts of inflammatory cytokines, such as interferon-gamma, tumor necrosis factor-alpha and granulocyte-macrophage colony stimulating factor (GM-CSF). AlloStim™ and methods of making AlloStim™ are described, for example, in U.S. Pat. No. 7,435,592, U.S. Pat. No. 7,678,572 and U.S. Pat. No. 7,402,431, all incorporated herein by reference. Other allogeneic or xenogeneic immune cells can also be used as components in the aTh2 composition. Some of the methods of the present disclosure are described with reference to AlloStim™ but this is not meant to limit the methods to the use of AlloStim™ only and other compositions may be used in the described methods.

The aTh1 compositions described herein may also include anti-viral or anti-retroviral medication (AVI composition). Compositions such as AlloStim™ which contain the necessary components of the aTh1 composition have been previously disclosed. In some embodiments, the use of AlloStim™ alone or aTh1 composition may not be sufficient for treating HIV infection. The AVI composition includes anti-retroviral medication together with the aTh1 composition.

While the aTh1 composition can be beneficial for cancer treatment, this composition may be detrimental to an HIV patient. This is due to the unique nature of the HIV life cycle. For example, when AlloStim™ is used as the aTh1 composition, intradermal injections of AlloStim™ can increase the titer of memory CD4+ cells specific for alloantigens. In HIV infection, this increase in CD4+ memory cells alone would only increase the number of CD4+ targets for the virus to infect. If the patient was not viral suppressed to have viral load below the limit of detection, circulating virions would infect the newly formed CD4 cells increasing the pool of latent virus. Thus, intradermal AlloStim™ injections alone will lead to increase latent viral pool. The feature of the present method that can protect these newly formed CD4+ cells from viral entry is a step that can activate these cells using intravenous infusions. Activated memory cells can be resistant to viral entry due to up-regulation of CCR5 agonist cytokines and down-regulation of the CCR5 receptor. However, the mass activation of memory cells can awaken the viral production of latently infected cells. Intravenous infusions of AlloStim™ can cause activation of T-cells and monocytes that can cause any latently infected cells to begin viral production. This can result in an increase in plasma viral load and can eventually lead to a decrease in CD4+ cell counts. Further, the activation of latent viral pools after intravenous AlloStim™ infusion and the subsequent increase in viral replication may lead to increased risks in the development of viral escape mutants that become resistant to HAART drug cocktails. Carefully sequenced administration by dose and route can be required in order to treat HIV using the aTh1 compositions such as AlloStim™, when combined with anti-retroviral medications such as used in HAART. This can slow the production of virus and can allow for establishment of immune control of the virus. Frequent monitoring of CD4 counts and HIV RNA viral load can be performed to assure the proper balance is maintained. The latent viral load can be monitored by monitoring both cellular and plasma viral DNA levels.

AlloStim™ or other aTh1 compositions can be used initially together with viral suppressing drugs to slow down the spread of virus to healthy cells and prevent viral mutation.

A variety of anti-retroviral drugs or medications can be included in the AVI composition. The AVI composition can include, for example, one or more drugs from any of the classes of antiretroviral drugs. The anti-retroviral drugs, for example, can include drugs from the following classes. Drugs from other classes are also within the scope of this description.

Nucleoside/Nucleotide Reverse Transcriptase Inhibitors (NRTIs): Sometimes called "nukes." These anti-HIV drugs can work to block HIV's ability to use reverse transcriptase to correctly change viral RNA into DNA. Host cells can use DNA to produce the proteins that the virus needs to make copies of itself.

Non-Nucleoside Reverse Transcriptase Inhibitors (NNRTIs): These are called "non-nukes." They can work in a very similar way to "nukes." Non-nukes also can block the enzyme, reverse transcriptase, and can also prevent HIV from making copies of its own DNA. But unlike the nukes (which work on the genetic material), non-nukes can act directly on the enzyme itself to prevent it from functioning correctly.

Protease Inhibitors (PIs): When HIV replicates inside cells, it can create long strands of its own RNA genetic material. These long strands have to be cut into shorter strands in order for HIV to create more copies of itself. The enzyme that acts to cut up these long strands is called protease. Protease inhibitors can block this enzyme and prevent those long strands of genetic material from being cut up into functional pieces.

Entry/Fusion Inhibitors: These medications can work to block the virus from entering cells. HIV attaches and bonds to CD4 cells through receptor sites. Receptor sites are found on both HIV and CD4 cells (they are found on other types of cells too). Fusion inhibitors can target those sites on either HIV or CD4 cells and can prevent HIV from "docking" into healthy cells. CCR5 is an example of a receptor site for HIV.

Examples of anti-HIV drugs that can be included in the AVI composition may include the following multi-class combinations: Atripla (efavirenz+tenofovir DF+emtricitabine); Complera (Eviplera, rilpivirine+tenofovir DF+emtricitabine); Stribild (formerly Quad) (elvitegravir+cobicistat+tenofovir DF+emtricitabine); Triumeq (formerly Trii) (dolutegravir+abacavir+lamivudine).

Examples of anti-HIV drugs include the following NNRTs: Edurant (rilpivirine, RPV, TMC-278); Intelence (etravirine, ETR, TMC-125); Rescriptor (delavirdine, DLV); Sustiva (Stocrin, efavirenz, EFV); Viramune and Viramune XR (nevirapine, NVP); Lersivirine (UK-453061).

Examples of anti-HIV drugs include the following NRTIs: Combivir (zidovudine+lamivudine, AZT+3TC); Emtriva (emtricitabine, FTC); Epivir (lamivudine, 3TC); Epzicom (Kivexa, abacavir+lamivudine, ABC+3TC); Retrovir (zidovudine, AZT, ZDV); Trizivir (abacavir+zidovudine+lamivudine, ABC+AZT+3TC); Truvada (tenofovir DF+emtricitabine, TDF+FTC); Videx EC and Videx (didanosine, ddI); Viread (tenofovir disoproxil fumarate, TDF); Zerit (stavudine, d4T); Ziagen (abacavir, ABC); Amdoxovir (AMDX, DAPD); Tenofovir alafenamide fumarate, TAF.

Examples of anti-HIV drugs include the following protease inhibitors: Aptivus (tipranavir, TPV); Crixivan (indinavir, IDV); Invirase (saquinavir, SQV); Kaletra (Aluvia, lopinavir/ritonavir, LPV/r); Lexiva (Telzir, fosamprenavir, FPV); Norvir (ritonavir, RTV); Prezista (darunavir, DRV); Reyataz (atazanavir, ATV); Viracept (nelfinavir, NFV); Prezcobix (Rezolsta, darunavir/cobicistat); Atazanavir+Cobicistat.

Examples of anti-HIV drugs include the following integrase inhibitors: Isentress (raltegravir, MK-0518); Tivicay (dolutegravir, S/GSK-72); Vitekta (elvitegravir, GS-9137).

Examples of anti-HIV drugs include the following fusion inhibitors: Fuzeon (enfuvirtide, ENF, T-20); Selzentry (Celsentri, maraviroc, UK-427,857)

The above stated anti-HIV drugs are exemplary and other anti-HIV drugs are within the scope of this description.

The aTh1 compositions and/or the AVI compositions described herein can be used in methods to reduce and or eliminate HIV from patients. The methods described herein can enhance the CD4+ cells in the patient. The methods can also reduce the viral load and/or purge the virus from the patient.

CD4 Enhancement Method

The methods included in the present description can include the CD4 Enhancement Method. The CD4 Enhancement Method can use the aTh1 composition in a HIV patient taking anti-viral medication. This can increase the CD4+ cell counts of HIV patients, preferably the Th1 memory (CD4+ CD45RO+) cells. The new CD4+ cells created by the method can be resistant to viral replication and viral entry. The CD4 Enhancement Method can be used in patients that have immunological failure on HAART medication.

The CD4 Enhancement Method can increase CD4+ cell counts by creating activated CD4+ Th1 memory cells in circulation. Activated CD4+ Th1 memory cells can be resistant to HIV replication. This HIV resistant state can be due to an increase in the production of chemokines that are released from activated memory cells which in turn interact with the CCR5 receptor (i.e., RANTES, MIP-1alpha and MIP-1beta) and due to the down-regulation of CCR5 expression on CD4 memory cells that are activated.

The creation of viral resistant CD4+ cells can be an important aspect of the CD4 Enhancement Method. Methods that would increase numbers of naïve CD4 cells, Th2 cells, Th0 cells or resting CD4 memory cells would only add "fuel to the fire". These undesirable CD4 subtypes are permissive for viral replication. "Fuel for the fire" means that there would be more CD4 targets for viral entry and thus more cells may be producing virions into plasma, which can lead to more cells with latent infection, increasing viral load and eventually resulting in increased CD4 cell death. Eventually the loss of CD4 cells would reduce the CD4 counts below the original baseline, causing the patient to be worse off than prior to the therapy.

The CD4 Enhancement Method can create high titers of activated Th1 memory cells that are resistant to viral entry and replication due to activation with CD28 co-stimulation (through the co-stimulatory ligands CD80 and CD86 ligands up-regulated on APC) that can cause an increase in expression of native CCR5 ligands and the concomitant down regulation of surface CCR5 expression. To create these HIV resistant cells, the method can include multiple injections of the aTh1 composition (priming doses) and activation of APC to express CD80 and CD86 co-stimulatory molecules. The priming doses of the aTh1 composition can be administered intradermally, subcutaneously, intramuscularly or intravenously. The aTh1 composition could also be administered by a combination of these routes.

In one embodiment, the aTh1 composition priming doses are administered multiple times intradermally. A minimum of two intradermal injections or doses can be required in order to cause memory cells to develop, such as about 4 or more doses are administered. The doses can generally be frequent. The doses may be administered up to about 2 weeks apart, or about 1 week apart, and even about 3-4 days apart. Doses less than about 2 days apart are integrated and still considered a single dose. Once CD4+ memory cells can be detected in the circulation, the patient can be said to be 'primed' (i.e., immune to the antigen(s) in the aTh1 composition).

The CD4 Enhancement Method can result in the increase in absolute CD4+ cell counts. The CD4/CD8 ratio may increase or remain near the same as baseline due to a concomitant increase in CD8 cells. In addition, the method can result in a shift in the Th1/Th2 balance to favor Th1. HIV infection causes a loss of Th1 cells resulting in Th2-dominated immune cells in circulation. The methods described herein can correct this imbalance by increasing the Th1 cell component.

In one embodiment, at least two doses of the aTh1 compositions are administrated in the same location. After at least two doses in the same location, a new location may be selected for administration of subsequent doses. Alternatively, all doses can be administered in the same location. If a new location is selected, at least two doses should be administered at each new location. This cycle of administering doses of aTh1 composition can continue until the desired CD4+ cell count is obtained.

Intradermal doses of the aTh1 composition in the same location can be administered to assure that professional antigen presenting cells (APC), such as Langerhan's cells (LC), macrophages (M) and immature dendritic cells (DC) that traffic to the injection site are exposed to the type 1 cytokines and CD40L in the aTh1 composition at the time they engulf the highly immunogenic antigen(s). It may take 2-3 days before these APC traffic to the administration site. After intradermal administration, LC of the skin can engulf and process the antigens from the aTh1 composition resulting in the activation and priming of antigen-specific T cells.

Type 1 cytokines and CD40L in the aTh1 composition can cause the professional APC that process the aTh1 antigen(s) to mature and express MHCI/II, CD80/86 and IL-12. These mature APC may then traffic to the draining lymph nodes to interact with naïve T-cells causing the activation, differentiation and proliferation of new effector CD4+ Th1 cells and CD8+ CTL (Tc1) killer cells specific for the antigen(s) in the aTh1 composition. Multiple administrations can convert the effector Th1/Tc1 cells to memory cells. In the presence of anti-retroviral drugs, as the administration of the number of doses of aTh1 composition increase eventually a new, higher CD4 set-point can be achieved. During the course of the aTh1 injections, CD4 counts and viral load can be monitored.

This CD4 Enhancement Method can result in the patient being 'primed' and immune to the antigen(s) in the aTh1 composition. This can result in an increase in memory CD4 cells that are resistant to viral entry upon activation. Multiple priming injections of the aTh1 composition are preferable. Such a 'pulsed' introduction of antigen to the immune system can cause an enhanced delayed-type hypersensitivity (DTH) response at the injection site. The DTH reactions are mediated by memory Th1 cells and the appearance of a DTH reaction at the injection site can confirm presence of CD4 memory cells specific for the aTh1 antigen(s). Increased DTH skin reaction can also correlate with increased titers of CD4 memory cells in the circulation of HIV+ patients.

The CD40L and type 1 cytokines in the aTh1 composition can non-specifically (polyclonally) activate memory T-cells. When memory Th1 cells are polyclonally activated, they can expand and maintain a HIV resistant memory, CCR5-phenotype. The expansion of HIV-resistant, CD4 memory cells can cause a beneficial sustained increase in CD4 counts. In order to polyclonally activate circulating CD4 memory cells, the aTh1 composition may be infused intravenously.

Intravenous infusion of aTh1 composition may also activate latently infected memory cells. These activated cells can begin to produce virus upon polyclonal activation. The method described herein can create a pool of memory CD4 cells resistant to virus, these cells can provide help for HIV-specific CTL killer cells to eliminate cells that are actively producing virus. If the patient remains on HAART medication, the viral production can be slowed so that the CD4 count can be maintained high enough to support the anti-HIV immune response. In this manner, the resident anti-HIV immune response can identify and kill the activated memory cells producing virus while new viral resistant memory cells are replacing these cells. This balance between immune elimination of activated cells producing virus and increase in viral-resistant memory cells eventually leads to an increase in absolute CD4 counts and a decrease in the latent viral burden. Fluctuations in CD4 counts may occur prior to reaching the higher CD4+ cells set point level.

After a patient is primed and the CD4 count has increased, the CD4 counts can be further increased and the memory cells can be continuously protected from HIV elimination by the simultaneous intradermal injection of the aTh1 composition and the intravenous infusion of the aTh1 composition. The polyclonal activation of Th1 memory cells in circulation can cause the establishment of a sustained type 1 cytokine storm. The intravenous infusion can cause activation of memory CD4 cells in the blood of HIV patients, which in turn can cause an increase in the production of type 1 inflammatory cytokines, creating a type 1 cytokine storm. Type 1 cytokines can polyclonally activate by-stander memory cells thus creating a positive feed-back loop for the maintenance of activated memory cells.

Activated memory cells can expand in the presence of type 1 cytokines, thus accelerating the increase in the circulating CD4 counts. A sudden and violent immune reaction is known to occur with a cytokine storm containing type 1 cytokines such as TNF-alpha and IFN-gamma. Such a cytokine storm can be beneficial to HIV patients. Also type I cytokines such as IFN-gamma and IL-12 can enhance the memory cell function and innate immune activity.

In preferred embodiments where the aTh1 composition used is AlloStim™, the intravenous infusion further enhances CD4 counts of HIV resistant memory cells due to the CD3/CD28 coated microbeads attached to the cells in this composition. These microbeads can also interact and activate host memory cells causing them to proliferate. Memory cells activated with CD3/CD28-coated microbeads can resist HIV infection.

In one embodiment, AlloStim™ cells are used as the aTh1 composition. The AlloStim™ cells are injected intradermally at a dose of between about $0.2 \times 10^6$ cells to about $2 \times 10^6$ cells, preferably about $1 \times 10^6$ cells. An intravenous preferred dose for accelerating CD4 counts is between about $1 \times 10^7$ and about $3 \times 10^7$ cells (low dose). AlloStim™ cells are suspended in buffer solution (e.g., PlasmaLyteA with 1% human serum albumin) at a concentration of about $1\times10^7$ cells/ml.

One method for accelerated CD4 count enhancement can include one or more low dose intravenous AlloStim™ infusions during the intradermal priming. The low dose intravenous infusions may occur within 7 days of the last intradermal injection, or within 24 hours, or at the same time as an intradermal injection. The intravenous dosing does not start until at least two intradermal priming doses have been administered, or after 4 intradermal priming doses or after more than 4 intradermal priming doses.

Variations on the timing, amounts and routes of administration can vary and all are within the scope of the present description.

Viral Load Reduction Method

The Viral Load Reduction Method can reduce viral load through enhancement of cellular immune control of the virus. This method can be useful in patients that are virological failures on HAART medication. The CD4 Enhancement Method and the acceleration of this method can also accomplish a reduction in viral load. However, the formed methods can require a resident anti-HIV immune response to exist that can be awakened by the increased CD4 counts. Some patients may not have an effective, resident anti-HIV immune response and thus are unable to mediate the immune elimination of cells that have been activated to produce virus. In this circumstance, the Viral Load Reduction Method can be helpful as it imprints the missing anti-HIV immune response so that the CD4 counts can be increased and the viral load decreased.

The Viral Load Reduction Method can include one or more HIV antigen components that are administered together with the aTh1 composition. The HIV antigen components can include, for example, whole attenuated virus, as well as natural or recombinant HIV viral proteins. These HIV antigens are administered together with the aTh1 composition at the same route and frequency of administration.

The HIV antigens and aTh1 composition are administered intradermally together or immediately following each other in a patient that has been previously primed. The aTh1 antigens can attract a vigorous memory response due to the prior priming. The viral antigens and the aTh1 antigens can then be engulfed by scavenger APC, such as LC or DC. These cells can process and present the antigens to activate HIV antigen-specific T-cells. By this method, the aTh1 composition together with the Th1 memory cells that arrive at the injection site due to the prior priming, can both act as an adjuvant to steer the development of Th1/Tc1 anti-HIV immunity.

The Viral Load Reduction Method generally includes HIV antigens for use together with the aTh1 composition. These HIV antigens can be natural or recombinant viral proteins, including tat, env and gp120. Whole attenuated virus or virus attenuated by nef substitution can also be used. The proteins can be expressed in a carrier such as pox virus. In a preferred embodiment, the HIV viral protein is the gag protein. The repeated administration of HIV antigens together with the aTh1 composition can establish high titers of CD4 Th1 memory cells and CD8 memory CTL specific for HIV. These memory cells can be maintained in an activated state by infusing the aTh1 composition intravenously.

Viral Purge Method

The Viral Purge Method can include escalating intravenous doses of the aTh1 composition in patients on anti-viral medication. This method is used in patients that have been first subjected to the CD4 Enhancement Method and/or the Viral Load Reduction Method. The Viral Purge Method is administered to patients that have achieved an increased CD4 set-point consisting of viral-resistant memory cells. If the patient has a high latent viral load, activation of these cells by intravenous infusion may cause a burst of viral release and may result in an immediate drop in CD4 counts. Thus it is safer to start the method from as high a CD4 set-point as possible. As an example, the patient is at a CD4 set-point >300 cells/ml, or at a set-point >500 cells/ml or at a set-point of >700 cells/ml.

In certain embodiments, patients that have been previously primed and have at least a 6 month history of viral load below the limit of detection are subjected to increasing intravenous doses of the aTh1 composition while maintaining active anti-viral suppression. The intravenous infusions can occur at least about 3 days apart. After each infusion, the viral load can be assayed to determine if a viral spike has occurred. A spike is any reading over the limit of detection. The doses of aTh1 can be increased at each infusion until a viral spike occurs. The appearance of a viral spike can be indicative that cells from the latent pool have been activated. After a viral spike occurs, the CD4 counts and viral load can be followed until the viral load returns to the undetectable level. When the viral load is undetectable, another IV infusion at the same dose as caused the viral spike can be administered. If again a viral spike is detected, the patient is followed until the viral load returns to baseline and the process can be repeated until no viral spike occurs after the intravenous infusion. At any time no viral spike is detected, the intravenous dose can be again escalated. If the escalated dose causes a viral spike, the process is repeated until no spike is produced. At the point that an escalated intravenous dose does not cause a viral spike, the intravenous dosing can be halted.

Once the intravenous doses are halted, the patient CD4 and viral load can be continued to be monitored. When the CD4 stabilizes with at least two counts a week apart above the baseline CD4 value and the viral load is undetectable, the patient can be taken off the anti-viral medication. While on a holiday from anti-viral medication the patient should be monitored for CD4 count and viral load. The patient should remain without anti-viral drugs until the viral load spikes. When the viral load spike occurs, the anti-viral medication should be started again immediately.

After the spike of viral load on anti-viral drug holiday, the process of escalating intravenous doses can be re-initiated. Each time the patient is placed on holiday from anti-viral medication, the time it takes for a viral spike to occur should be increased.

In embodiments where AlloStim™ is used as the aTh1 composition, the escalating intravenous dosing can start at about $3\times10^7$ cells and can escalate to about $5\times10^7$ cells to about $10\times10^7$ cells to about $15\times10^7$ cells to about $20\times10^7$ cells. Dose escalation can continue at intervals of $5\times10^7$ cells to a maximum of $100\times10^7$ cells.

As discussed above, combinations of the CD4 enhancement method, the viral load reduction method and the viral purge method can be administered. In some embodiments, the patient is administered HAART as appropriate in conjunction with the aTh1 composition.

EXAMPLES

Example 1

During the initial protocol treatment phase, patients are kept on HAART therapy. After detecting a spike in viral burden, indicating successful activation of latent virus, followed by a decrease in viral burden to baseline, indicating immune control patients can be eligible for the HAART interruption phase.

To minimize the risk of treatment interruption, patients are closely monitored and resume treatment should virus replication be detected.

The protocol alters between intradermal and escalating intravenous dosing of AlloStim™ in patients on HAART. The intradermal dosing is designed to increase the titer of circulating CD4+ Th1 memory cells that are resistant to HIV infection. The intravenous infusion is designed to provide an inflammatory cytokine storm and activate memory CD4 cells and macrophages (through CD40-CD40L). Activation should stimulate latent virus replication within these reservoirs. In addition, the intravenous infusion should activate NK cells which will target and kill viral replicating cells providing a source of viral antigens. Dendritic cells will process the shed viral antigens and in the inflammatory environment stimulate anti-HIV-specific immunity. The continuous inflammatory storm will disable viral immunoavoidance mechanisms permitting clearance of cells with replicating virus The cycling between intradermal injections to increase CD4 cells and intravenous infusions to activate latent virus and stimulate anti-HIV immunity is expected to clear latent virus. Each IV infusion should cause a spike in viral load and subsequent immune control should then gradually decrease viral load. If there is difficulty in returning viral loads to baseline viral blocker drugs will be added (such as Maraviroc and/or Fuzeon).

Regimen

The initial protocol is 28 days.
Day 0: Intradermal AlloStim™
Day 3: Intradermal AlloStim™
Day 7: Intravenous AlloStim™ (1 ml)
Day 10: Intradermal AlloStim™
Day 14: Intradermal AlloStim™
Day 17: Intravenous AlloStim™ (3 ml)
Day 21: Intradermal AlloStim™
Day 24: Intradermal AlloStim™
Day 28: Intravenous AlloStim™ (5 ml)

Viral load and CD4/CD8 ratio is measured at baseline (Day 0) and Days 10, 21 and 29) and every 28-32 days thereafter for 6 months.

Research blood (45 ml) is drawn at or before baseline (Day 0) and Day 7, 17, 27 before IV infusions. PBMC and plasma is stored frozen until analyzed for Th1/Th2 balance (ELISPOT), HIV-specific immunity (ELISPOT), cytokine bead array.

Phenotype analysis is conducted prior to baseline and Day 60 (+/−2 days) including:
CD3, CD4, CD8, CD45RA, CD45RO, CD62L, CD25
CD14, HLA-DR, CD80, CD86, CD16, CD38, CD117
CBC, CMP, CRP laboratory tests for safety taken at baseline, Day 7, Day 14, Day 21 and Day 28.

HAART Interuption

Access to lymphoid tissue or most anatomic compartments in otherwise healthy HIV subjects in order to determine level of latent infection is difficult. Further, even if such studies fail to detect an infected reservoir, they cannot prove latent virus eradication. The ultimate test of efficacy can only be the withdrawal of HAART.

Patients that experience a spike in viral load and then recover to baseline or lower and remain at base line or lower for at least 60 days are provided the option of entering into a HAART interruption phase of the protocol. In this phase, all viral suppressive drugs are withdrawn and viral load will be measured daily for the first 7 days. If an increase in viral load is detected, HAART will be re-started. If no rise in viral load is detected, the HAART interruption is continued with viral load being measured weekly for 7 weeks. If no viral load increase is detected, monthly viral burden tests are conducted until the 1 year anniversary of the HAART interruption. At any time an increase in viral burden is detected, HAART is reinitiated.

Primary Outcome Measures:

Changes in steady state viremia (so-called viral set point) at baseline and monthly for 6 months after completion of 28 day protocol while remaining on HAART.

Safety and tolerability

Changes from baseline and absolute counts and activation status of CD4 and CD8 naïve and memory T cells Changes in absolute counts and activation state of monocyte/macrophages Changes in the number of interferon (IFN)-gamma generating (in response to HIV antigens) CD4 T cells/million peripheral blood mononuclear cells (PBMCs) as measured by intracellular cytokine staining (ICS) or ELISPOT.

Secondary Outcome Measure:

Time to viral burden increase from baseline after HAART interruption

Inclusion Criteria:

HIV-1-infected

On a stable HAART regimen without changes or interruptions for at least 12 weeks. prior to study entry. Patients must be currently taking regimens containing drugs of at least two different classes.

Two readings of plasma HIV-1 viral load of less than 50 copies/ml within 30 days prior to study entry.

CD4 count greater than 350 cells/mm^3 within 12 weeks prior to study entry.

Lowest CD4 count greater than 250 cells/mm^3 at any time prior to study entry.

Willing to use acceptable forms of contraception.

Karnofsky performance score 90 or higher obtained within 30 days prior to study entry.

Exclusion Criteria:

Age<18 years old.

Patients with failure to HAART.

HIV-1 viral load greater than 500 copies/ml within the 24 weeks prior to study entry.

History of any chronic autoimmune disease (e.g., Graves' disease). Excessive exposure to the sun (e.g., sunbathing, tanning bed) within 2 weeks prior to study entry.

Previous CDC Category B or C event.

Use of immunomodulating therapy, including cyclosporine, IgG-containing products, interleukins, interferons, or systemic glucocorticosteroids (including those inhaled) within 6 months prior to study entry.

Exposure to an experimental HIV vaccine.

Any vaccine within 30 days prior to study entry.

Investigational products within 12 weeks prior to study entry.

Current drug or alcohol use or dependence that, in the opinion of the investigator, would interfere with the study.

Serious illness requiring systemic treatment and/or hospitalization. Participants who complete therapy or are clinically stable on therapy for at least 14 days prior to study entry are not excluded.

Positive hepatitis B surface antigen or positive anti-hepatitis C antibody at screening.

Pregnant or breastfeeding.

Adequate organ function including:

Marrow:

Platelets>100,000/mm$^3$.

Absolute neutrophil count≥1,500/mm$^3$.

Hemoglobin≥10.0 g/dL (transfusion allowed)

Hepatic:

Serum Total bilirubin<1.5×ULN mg/dL,

ALT (SGPT)/AST (SGOT)≤1×upper limit of normal (ULN).

Renal:

Serum creatinine (SCR)<1.0×ULN, or

Creatinine clearance (CCR)>30 mL/min.

History of cardiac, pulmonary, gastrointestinal, hepatic, renal, pancreatic, or neurologic disease which, in the opinion of the study official, will compromise study participation Example #1

A HIV+ man on HAART medication for 19 years with viral load always below detectable limits was entered into the Viral Enhancement protocol.

The patient had absolute CD4 cell counts of 250-350 at baseline.

He was administered 1×10$^7$ AlloStim™ intradermally while on his HAART medication on Day 0, Day 3 in same location. Then again on Day 7 and Day 10 in another location. Over this period of time, his absolute CD4 count increased from 350 cells to 450 cells.

Beginning on day 14 escalating intravenous doses of AlloStim™ were administered. On day 14, 1×10$^7$ cells were infused. There was no detectable viral load. On day 17, 5×10$^7$ cells were infused. There was no detectable viral load. On Day 21, 10×10$^7$ cells were infused. The viral load spiked to 66 and remained above detection for 10 days when it again returned to undetectable. CD4 count increased to over 500 during this period and continued to rise over the next 60 days stabilizing at over 600.

Example #1

A HIV positive man on HAART medication for at least six years with undetectable viral load. His absolute CD4 counts ranged from 100-230 over a period of 2 years.

The patient had a 250 CD4 count at baseline.

He was administered 1×10$^7$ AlloStim™ intradermally on Day 0, Day 3, Day 10 and Day 14. His CD4 counts increased to 293. On Day 17 he received a 1×10$^7$ intradermal injection and a 3×10$^7$ intravenous infusion. On day 21 he received a 1×10$^7$ intradermal injection and a 10×10$^7$ intravenous infusion. On Day 24 he received a 10×10$^7$ intravenous infusion. On Day 28 and day 31 he received a 10×10$^7$ intravenous infusion. His viral load spiked at 300 on day 31 and returned to baseline by day 42. During this time his CD4 counts slowly declined to below 200 by day 42.

Beginning on Day 49 until Day 63, he received 1×10$^7$ intradermal injection of AlloStim every 3-4 days. His CD4 count gradually increased from below 200 to above 300. His viral remained undetectable.

On Day 84, Day 87, Day 91 and Day 94 he received 10×10$^7$ intravenous AlloStim™ infusions. On Day 97 his viral load spiked to 86. By Day 101, his viral load returned to baseline and his CD4 counts remained over 300. He was removed from his HAART medication.

He remained with undetectable viral load for 31 days without HAART medication. On Day 32 the viral load was 300 and CD4 230. HAART was restarted and the viral came back to undetectable and CD4 stabilized at around 250.

Although the present description has been described with reference to preferred embodiments, workers skilled in the art will recognize that changes may be made in form and detail without departing from the spirit and scope of the invention.

What is claimed is:

1. A kit comprising components of a therapeutic human immunodeficiency virus (HIV) immunogenic composition, wherein the kit comprises:
   an intradermal aTh1 composition comprising at least two intradermal doses;
   an intravenous aTh1 composition comprising at least two intravenous doses, the intravenous doses packaged separately with escalating doses of the aTh1 composition in each package, wherein the package with the smallest amount of the intravenous, aTh1 composition is the first intravenous dose and each subsequent intravenous dose has an escalated amount of the aTh1 composition than the preceding intravenous dose;
   components of highly active antiretroviral therapy (HAART); and
   one or more HIV antigens.

2. The kit of claim 1 wherein the intradermal composition is divided into single dose packages with the same amount of the intradermal composition in each package.

3. The kit of claim 1 wherein the intravenous composition comprises at least three doses divided into single dose packages, wherein the second dose of the intravenous aTh1 composition has an escalated does relative to the first dose of the intravenous aTh1 composition and the third dose of the intravenous aTh1 composition has an escalated dose relative to the second dose of the intravenous aTh1 composition.

4. The composition of claim 1 wherein the aTh1 composition comprises activated CD4+ T-cells and increases CD4+ cell counts in an individual by creating activated CD4+ Th1 memory cells in circulation in the individual.

5. A composition comprising:
   an aTh1 immunogenic composition comprising an alloantigen, a molecule that interacts with CD40 surface receptor and Type I cytokines;
   at least one or more anti-retroviral drugs; and
   at least one or more HIV-antigens, wherein administration of the aTh1 immunogenic composition to a patient leads to activation of latently infected memory cells in the patient.

6. An AVI composition comprising:
   an aTh1 immunogenic composition comprising an alloantigen, a molecule that interacts with CD40 surface receptor and Type I cytokines; and
   at least one or more anti-retroviral drugs, wherein administration of the aTh1 immunogenic composition to a patient leads to activation of latently infected memory cells in the patient.

7. The composition of claim 6 further comprising one or more HIV antigens.

8. The composition of claim 5 wherein the aTh1 composition comprises activated CD4+ T-cells and increases CD4+ cell counts in an individual by creating activated CD4+ Th1 memory cells in circulation in the individual.

9. The composition of claim 6 wherein the aTh1 composition comprises activated CD4+ T-cells and increases CD4+ cell counts in an individual by creating activated CD4+ Th1 memory cells in circulation in the individual.

* * * * *